US00PP22397P2

(12) United States Plant Patent
Uebelhart

(10) Patent No.: US PP22,397 P2
(45) Date of Patent: Dec. 20, 2011

(54) ***RUDBECKIA* PLANT NAMED 'LITTLE GOLDSTAR'**

(50) Latin Name: *Rudbeckia fulgida*
Varietal Denomination: Little Goldstar

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 0 days.

(21) Appl. No.: 12/932,921

(22) Filed: Mar. 9, 2011

(51) Int. Cl.
*A01H 5/00* (2006.01)

(52) U.S. Cl. ..... Plt./474

(58) Field of Classification Search ..... Plt./474
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of hybrid *Rudbeckia,* 'Little Goldstar', characterized by its dwarf plant habit, its numerous inflorescences from mid summer through fall, its foliage with narrow leaves, its basal leaves that remain healthy and green during flowering, and its vigorous growth habit.

2 Drawing Sheets

Botanical classification: *Rudbeckia fulgida.*
Variety denomination: 'Little Goldstar'.

BACKGROUND OF THE INVENTION

The present invention relates to a new and distinct cultivar of *Rudbeckia* plant, botanically known as *Rudbeckia fulgida* and will be referred to hereinafter by its cultivar name, 'Little Goldstar'.

'Little Goldstar' was derived from a controlled breeding program conducted by the Inventor at a nursery in Schwamstedt, Germany. 'Little Goldstar' was selected in summer of 2009 by the Inventor as a single unique plant derived from a cross made in 2007 between unnamed plants from his breeding program with the female parent identified with accession No. GU2004 and the male parent identified with accession No. R06012.

Asexual reproduction of the new cultivar was first accomplished via in vitro propagation under the direction of the Inventor in Heerhugowaard, The Netherlands in August 2009. The characteristics of this cultivar have been determined to be stable and are reproduced true to type in successive generations.

SUMMARY OF THE INVENTION

The following traits have been repeatedly observed and are determined to be the characteristics of the new cultivar of *Rudbeckia.* These attributes in combination distinguish 'Little Goldstar' as unique from all other varieties of *Rudbeckia* known to the Inventor.

1. 'Little Goldstar' exhibits a dwarf plant habit, reaching 25 to 30 cm in height.
2. 'Little Goldstar' produces numerous inflorescences from mid summer through fall.
3. 'Little Goldstar' exhibits foliage with narrow leaves.
4. 'Little Goldstar' exhibits basal leaves that remain healthy and green during flowering.
5. 'Little Goldstar' exhibits a vigorous growth habit.

'Little Goldstar' can be compared to its parent plants. The female parent differs from 'Little Goldstar' in being much less vigorous. The male parent differs from 'Little Goldstar' in being less floriferous. 'Little Goldstar' can also be compared to *Rudbeckia* cultivars 'Goldsturm' (not patented), 'City Garden' (not patented) and 'Early Bird Gold' (U.S. Plant Pat. No. 20,286), which all differ in being taller in height with average heights reaching about 100 cm versus a height of up to 30 cm for 'Little Goldstar' and in being less floriferous by producing an average of 40 inflorescences versus 80 inflorescences as observed for 'Little Goldstar'. 'Goldsturm' also differs in having basal leaves that fade to a yellowish brown color during the flowering period, whereas the basal leaves of 'Little Goldstar' remain healthy and green.

BRIEF DESCRIPTION OF THE DRAWINGS

The accompanying colored photographs illustrate the overall appearance and distinct characteristics of the new *Rudbeckia.* The photographs were taken of plants grown for six months in a greenhouse in 5-liter container from a 5 cm plug in Rijswijk, The Netherlands.

The photograph in FIG. 1 is a side view of 'Little Goldstar' in bloom.

Figure 1:
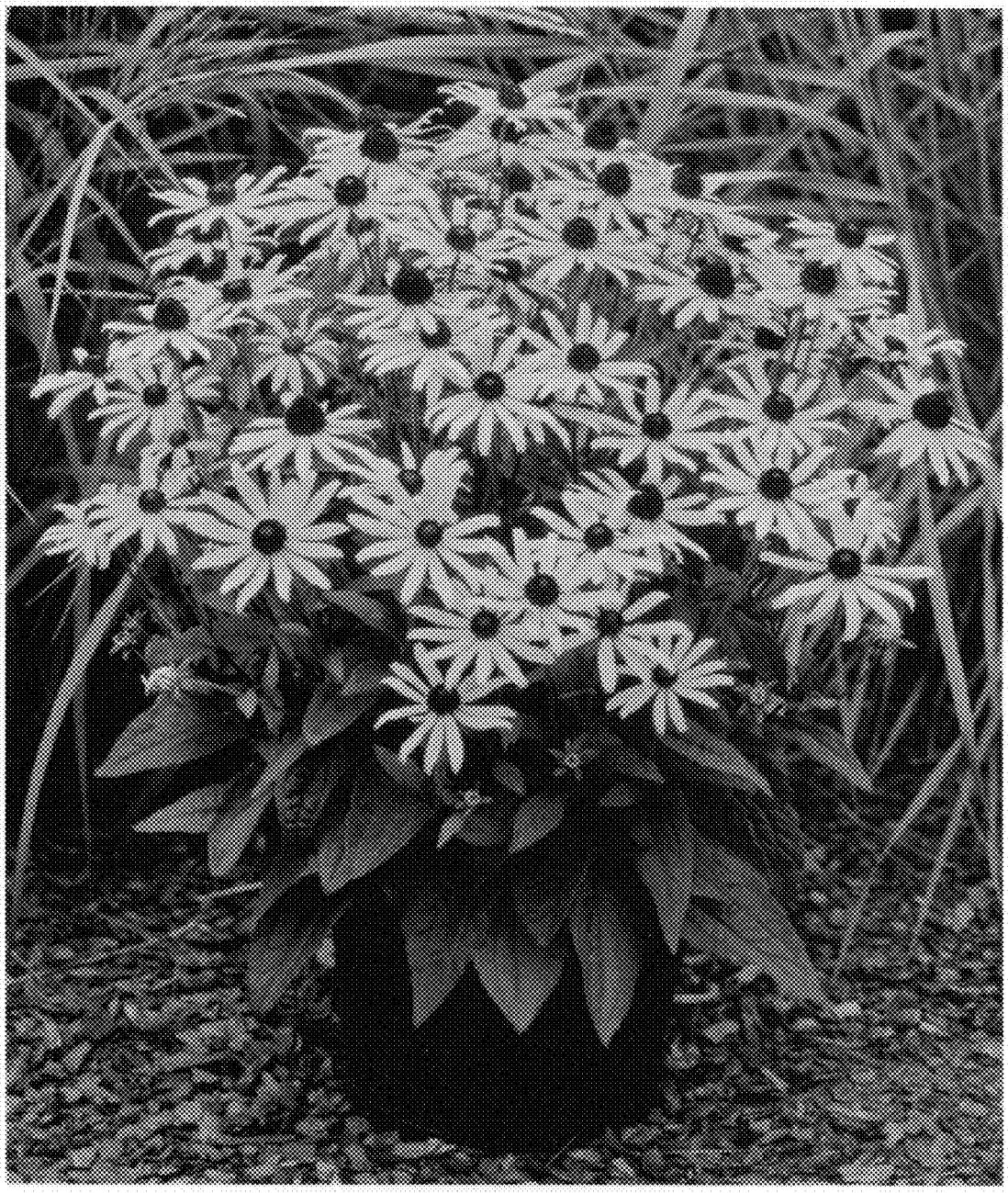
Figure 2:
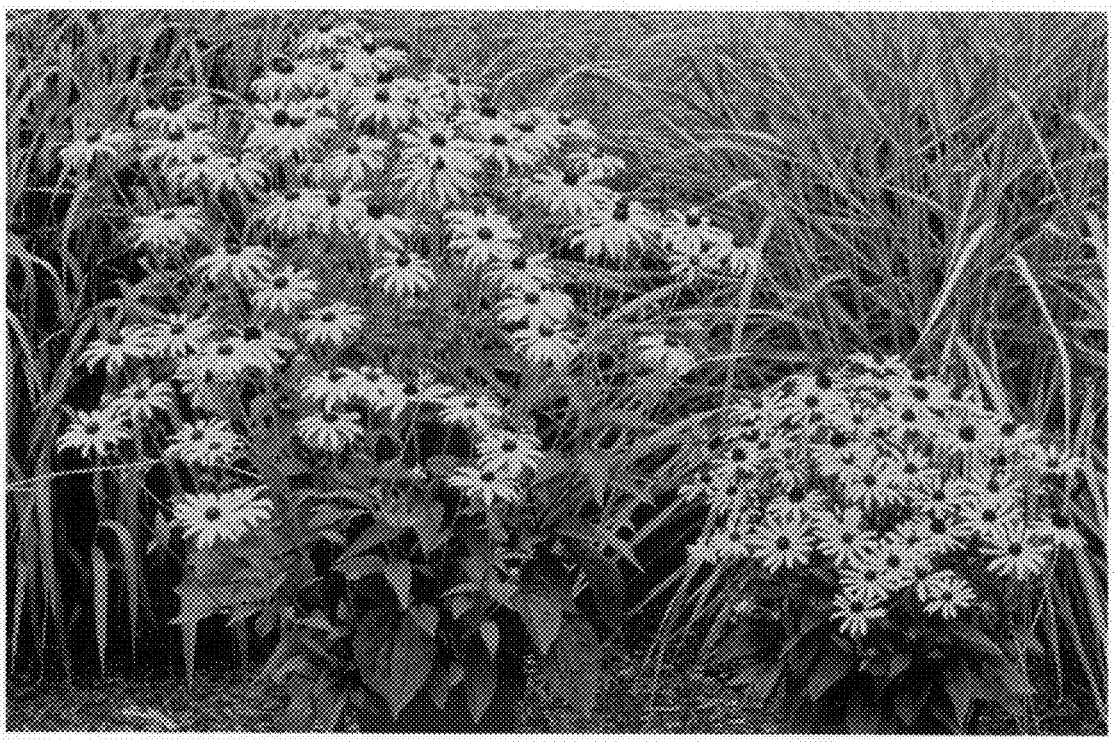

The photograph in FIG. 2 provides a comparison between 'Goldsturm' on the left and 'Little Goldstar' on the right.

Figure 3:
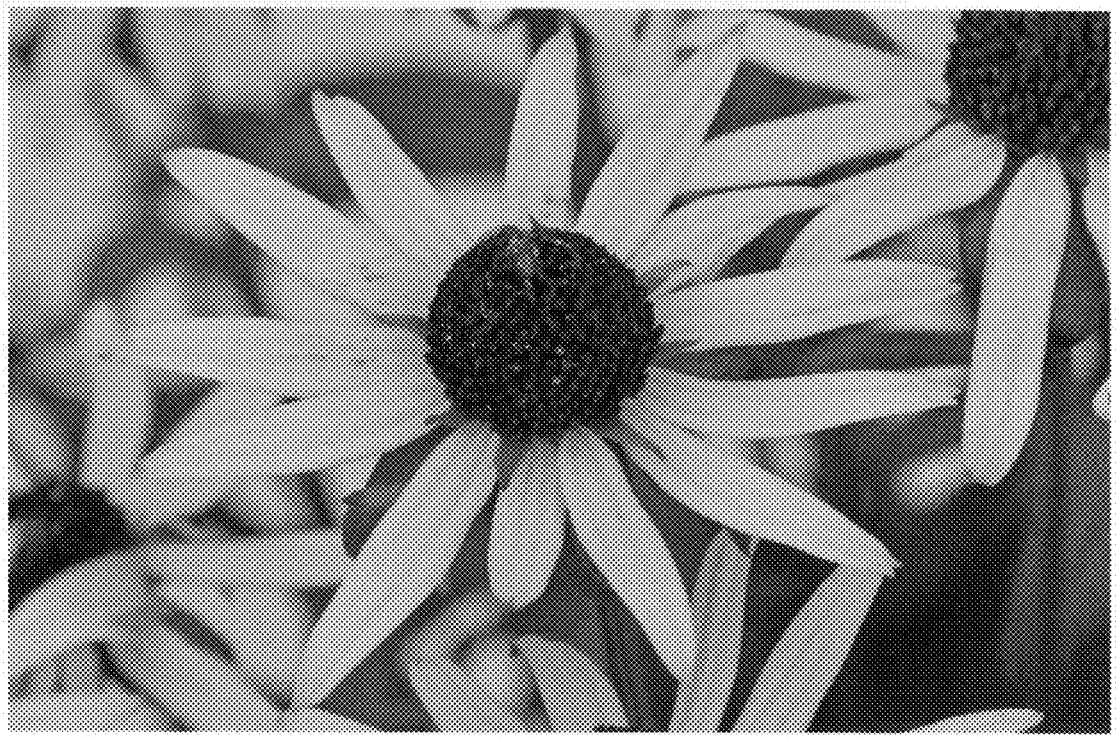

The photograph in FIG. 3 provides a close-up view of the inflorescences of 'Little Goldstar'. The colors in the photographs may differ slightly from the color values cited in the detailed botanical description, which accurately describe the colors of the new *Rudbeckia.*

BOTANICAL DESCRIPTION OF THE PLANT

The following is a description of the new cultivar as observed for three years as grown in a trial plot in Schwamstedt, Germany with the detailed botanical data taken from plant grown for six months in a greenhouse in 5-liter container from a 5 cm plug for in Rijswijk, The Netherlands. The phenotype of the new cultivar may vary with variations in environmental, climatic, and cultural conditions, as it has not been tested under all possible environmental conditions. The color determination is in accordance with The 2007 R.H.S.

Colour Chart of the Royal Horticultural Society, London, England, except where general color terms of ordinary dictionary significance are used.

General description:

*Blooming period.*—Continuously from July to October in Schwamstedt, Germany.

*Plant habit.*—Herbaceous perennial, clump-forming, upright, dwarf.

*Height and spread.*—Reaches about 30 cm in height and 50 cm in spread in 3 years (20 cm in height and 40 cm in height in 2 years).

*Hardiness.*—U.S.D.A. Zones 3 to 8.

*Diseases and pests.*—No susceptibility or resistance to diseases or pests has been observed.

*Root description.*—Fibrous.

Growth and propagation:

*Propagation.*—Division and tissue culture.

*Growth rate.*—Vigorous, an average of 8 cm per month in the spring.

Stem description:

*Shape.*—Rounded.

*Stem color.*—143A.

*Stem size.*—Average of 3.5 mm in diameter and an average of 19 cm in height.

*Stem surface.*—Moderately covered with short strigose hairs about 1.5 mm in length and close to NN155C to NN155D in color.

*Stem number.*—Average of 9 main stems.

*Internode length.*—An average of 3.7 cm in length.

*Branching.*—Main stems grow from the base.

Foliage description:

*Leaf shape.*—Ovate to narrowly ovate.

*Leaf division.*—Simple.

*Leaf base.*—Attenuate to cuneate.

*Leaf apex.*—Acute.

*Leaf venation.*—Pinnate, tri-nerved, upper surface 137A to 147A in color, lower surface 144B to 144C in color.

*Leaf margins.*—Un-deeply serrate.

*Leaf attachment.*—Petiolate.

*Leaf arrangement.*—Alternate.

*Leaf size.*—Average of 9 cm in length and 3.8 cm in width.

*Leaf color.*—Young upper surface; blend of 137A and 147A, young lower surface; blend of 137C and 138A, mature upper surface; blend of 137A and 147A, mature lower surface; 147B.

*Leaf surface.*—Upper surface slightly glossy, rugose, main veins carinate, rough to touch, moderately pubescent with short strigose hairs with an average length of 0.5 mm, 155C to 155D in color, lower surface is dull, main veins carinate, slightly rough to touch, sparsely pubescent with white short strigose hairs with an average length of 0.5 mm and 155C to 155D in color, leaf color of basal leaves is retained when in bloom.

*Petioles.*—Typically about 3 mm in length, 3 mm in width and v-shaped, upper surface; smooth, blend of 143B and 137A in color, margins sparsely covered with white short strigose hairs with an average length of 0.5 mm and about 155C to 155D in color, lower surface; smooth, 144B in color.

Flower description:

*Type.*—Terminal capitulum, consisting of ray florets and disc florets.

*Capitulum number.*—Two terminal capitulum per stem, up to 80 capitulums on a 3 year-old plant.

*Lastingness of inflorescence.*—About 10 days.

*Capitulum size.*—Matures to about 3.4 cm in height and 64 cm in diameter, disk size is about 2.7 cm in diameter.

*Fragrance.*—Very faint, somewhat moldy smell, not unpleasant.

*Involucral bracts or phyllary.*—Cuneate base, acute apex, narrow ovate in shape, entire margin, dull and smooth, about 18 arranged in two rows, upper row; 1.1 cm in length and 3 mm in width, 137A in color on both upper and lower surfaces, lower row; 1.8 cm in length and 4 mm in width, 137C in color on both upper and lower surfaces.

*Receptacle.*—Ovate in shape, about 9 mm in height and 6 mm in diameter, 145D in color.

*Buds.*—Globular in shape, up to 1 cm in length and 1.7 cm in diameter, immature ray florets are 150B in color and immature disk flowers appear 200A in color.

*Peduncle.*—Strong, straight on top of main flowering stem, 144B in color, texture is rough with short strigose white hairs, average of about 1 mm in length and 155C to 155D in color, terminal peduncle; typically 14.5 cm in length and an average of 3 mm in diameter, fourth peduncle; typically 9 cm in length and an average of 3 mm in diameter.

*Ray Florets.*—About 12, between narrow elliptic and narrow oblanceolate in shape, vertical ridges on both surfaces, about 3.1 cm in length and 7 mm in width, between acute and praemorse apex, cuneate base, entire margin, smooth and dull in texture, average angle varyies between −10° and +10°, color of upper surface when just opening; blend of 17A to 17B and lighter towards the apex 17C, color of lower surface when just opening; 17C with the center tinged 154A to 154B, color of upper surface fully open; 17A blending with 17C towards the apex, color of lower surface fully open; 15B, upper surface fades to 17A in color, lower surface fades to 15B in color.

*Disk florets.*—Average about 320, slightly curved and tubular in shape, arranged spirally on a conical receptacle, about 8 mm in length and 1.5 mm in width, tubular in shape with a free apex, entire margins, fused base, color of upper and lower surface when just opening and fully open; apex 200A mid-section, mid-section color fades to 145C, base 158D.

Reproductive organs:

*Gynoecium.*—Pistil; 1, 5 mm in length, style; 4 mm in length, between 186C to 186D in color, stigma; decurrent, 186C blending into 200A in color, ovary; 144A in color.

*Androcoecium.*—Stamens; 2, filaments; 2 mm in length, 200A in color, anther; short oblong in shape, 1 mm in length, 200A in color, pollen; low in quantity and 14A to 14B in color.

*Fruit/seed.*—None observed.

It is claimed:

1. A new and distinct cultivar of *Rudbeckia* plant named 'Little Goldstar' substantially as herein illustrated and described.

* * * * *